United States Patent
Bodenstaff et al.

(10) Patent No.: US 7,916,294 B2
(45) Date of Patent: Mar. 29, 2011

(54) SYSTEM AND METHOD FOR SOLUBILITY CURVE AND METASTABLE ZONE DETERMINATION

(75) Inventors: Emilio René Bodenstaff, Delft (NL); Danny Dirk Pieter Willem Stam, Den Haag (NL); Benjamin McKay, Amsterdam (NL); Mimoun Lamkadmi, Rotterdam (NL)

(73) Assignee: Avantium International B.V., Amsterdam (NL)

( * ) Notice: Subject to any disclaimer, the term of this patent is extended or adjusted under 35 U.S.C. 154(b) by 270 days.

(21) Appl. No.: 12/067,827

(22) PCT Filed: Sep. 21, 2006

(86) PCT No.: PCT/NL2006/000466
§ 371 (c)(1),
(2), (4) Date: Jun. 30, 2008

(87) PCT Pub. No.: WO2007/035087
PCT Pub. Date: Mar. 29, 2007

(65) Prior Publication Data
US 2008/0252886 A1    Oct. 16, 2008

(30) Foreign Application Priority Data
Sep. 22, 2005 (WO) .................. PCT/NL2005/000688

(51) Int. Cl.
*G01N 21/51* (2006.01)
*G01N 21/59* (2006.01)
*G06F 19/00* (2011.01)

(52) U.S. Cl. ......... 356/337; 356/441; 356/432; 702/189

(58) Field of Classification Search .................. 356/244, 356/246, 432–440, 72–73, 335–344; 73/61.63, 73/53.03, 61.41; 374/17–20, 27–28
See application file for complete search history.

(56) References Cited

U.S. PATENT DOCUMENTS

| | | | |
|---|---|---|---|
| 3,643,492 A * | 2/1972 | Simpson | .......................... 374/23 |
| 3,677,064 A * | 7/1972 | Simpson | .......................... 374/25 |
| 3,807,865 A | 4/1974 | Gordon et al. | |
| 3,875,788 A | 4/1975 | Mills | |
| 4,188,311 A * | 2/1980 | Aalbers et al. | ................. 510/426 |
| 4,674,329 A * | 6/1987 | Mulder | ....................... 73/304 C |

(Continued)

FOREIGN PATENT DOCUMENTS
DE    19935830 A1    2/2001
(Continued)

OTHER PUBLICATIONS

English Abstract of JP H4-145365.

*Primary Examiner* — Sang Nguyen
(74) *Attorney, Agent, or Firm* — Hoffmann & Baron, LLP

(57) ABSTRACT

A system for determining a solubility of a substance comprises a holder to hold a sample comprising an amount of the substance and an amount of the solvent system. The system further comprises a temperature conditioner to alter a temperature of the sample, an optical measurement device to measure an optical parameter of the sample and a control device to control at least the temperature conditioner and the optical measurement device. The control device may be programmed to alter the temperature of the sample by the temperature conditioner, measure the optical parameter of the sample by the optical measurement device, and determine the solubility of the substance from a change of the optical parameter of the sample as a function of the temperature.

46 Claims, 4 Drawing Sheets

U.S. PATENT DOCUMENTS

| | | | | |
|---|---|---|---|---|
| 4,804,274 A | * | 2/1989 | Green | 374/17 |
| 4,883,958 A | * | 11/1989 | Vestal | 250/288 |
| 5,088,833 A | * | 2/1992 | Tsang et al. | 374/17 |
| 5,758,968 A | * | 6/1998 | Diebold | 374/17 |
| 6,717,665 B2 | * | 4/2004 | Wagner et al. | 356/244 |
| 7,075,652 B1 | * | 7/2006 | Sarvazyan et al. | 356/432 |
| 7,140,239 B2 | * | 11/2006 | Greenwood et al. | 73/61.63 |
| 2001/0005593 A1 | | 6/2001 | Kawamura | |
| 2001/0006807 A1 | | 7/2001 | Bray et al. | |

FOREIGN PATENT DOCUMENTS

| | | |
|---|---|---|
| EP | 0102106 A1 | 3/1984 |
| EP | 1215483 A1 | 6/2002 |
| JP | 4145365 | 5/1992 |

* cited by examiner

SYSTEM AND METHOD FOR SOLUBILITY CURVE AND METASTABLE ZONE DETERMINATION

CROSS-REFERENCE TO RELATED APPLICATIONS

This application is the National Stage of International Application No. PCT/NL2006/000466; filed Sep. 21, 2006, which claims the benefit of International Application No. PCT/NL2005/000688, filed Sep. 22, 2005, the contents of which is incorporated by reference herein.

FIELD OF THE INVENTION

This invention relates to a system and method for the determination of solubility curves and metastable zone widths for a substance in a solvent or mixture of solvents (the solvent system).

BACKGROUND OF THE INVENTION

[Solubility Measurement] Considerable prior art exists regarding the measurement of the solubility of a material by performing experiments, e.g. dissolving an amount of a substance in an amount of a solvent system to test the solubility of the substance in the solvent system. A number of parameters may be varied, such as the temperature at which the experiment takes place, the ratio of the amount of substance to the amount of the solvent system, the duration of the experiment, the method of agitation used to obtain a homogeneous mixture of the substance and the solvent system e.g. stirring or shaking, the workup method e.g. centrifugation, and the analytical techniques used to determine the amount of dissolved material.

[Turbidity Measurement & "Optical Parameter"] Further, the prior art comprises a number of methods for assessing whether a substance has been fully dissolved in a solvent system by measuring an optical parameter of the sample. This optical parameter is related to the amount of suspended solids present in the sample. This may involve measuring the attenuation, by means of scattering or absorbance, of a beam of optical light directed through a portion of the sample. Alternatively, this may involve measuring the intensity of scattered light at a detector placed at an angle to the optical light source directed through a portion of the sample. Furthermore, one or more light beams and one or more detectors may be used. Optical light is understood to include the infrared, visible or ultraviolet regions of the electromagnetic spectrum. Alternatively, the quantity of dissolved material may be determined by removing a portion of the sample and analysing it gravimetrically or by using spectroscopic or ultrasonic methods. The quantity of dissolved material may also be determined in situ using spectroscopic or ultrasonic methods or electrozone sensing.

["Solubility Curve" And "Metastable Zone"] Solubility and metastable zone width curves are known as a method for summarising and graphically representing the range of conditions under which crystals will grow and those conditions that will result in primary nucleation. FIG. 2 depicts an example of a solubility curve and the corresponding metastable zone. In FIG. 2, the temperature TEMP is on the horizontal axis and the concentration of the material CONC is on the vertical axis of the graph. The line indicated by SOL in FIG. 2 is the solubility curve. A solubility curve indicates the solid-liquid thermodynamic equilibrium concentration of a substance in a solvent system, as a function of temperature. It is also referred to as the clear point curve in the prior art, as it can be obtained experimentally by heating a slurry of material in a solvent system until complete dissolution is obtained, resulting in a clear solution (the clear point). Crystals will grow at concentrations above the solubility curve. The line indicated by MSZ in FIG. 2 is the metastable zone boundary. The metastable zone boundary indicates the concentration of a substance in a solvent system above which primary nucleation occurs, as a function of temperature. It is also referred to as the cloud point curve in the prior art, as it can be obtained experimentally by cooling a saturated solution at a fixed rate until nucleation occurs and the solution becomes cloudy (the cloud point). At concentrations above the metastable zone boundary, spontaneous crystallisation, i.e. primary nucleation, will occur.

SUMMARY OF THE INVENTION

[Objective] An object of the present invention is, therefore, to provide an improved system and method for automating the required experimentation and data analysis for generating solubility curves, identifying the metastable zone width and reporting the results.

[The System] The system according to the invention, comprises a holder to hold a sample comprising an amount of the substance and an amount of the solvent system, a temperature conditioner to alter the temperature of the sample, an optical measurement device to measure an optical parameter of the sample, a control device to control at least the temperature conditioner and the optical measurement device and the control device being programmed to:

a) alter the temperature of the sample by the temperature conditioner;
b) measure the optical parameter of the sample by means of the optical measurement device; and
c) determine the clear points and cloud points of the sample from changes of the optical parameter of the sample as a function of the temperature.

As the control device controls at least the temperature conditioner and the optical measurement device, automated experiments may be performed, e.g. altering the temperature of a sample, measuring the optical parameter and so deriving clear points and cloud points. The system may further include a stirrer e.g. a magnetic stirrer or overhead stirrer, to stir the sample, which may also be controlled by the control device. As the stirrer may be controlled by the control device, stirring may e.g. be varied for various measurements, or be dependent on a parameter, such as a temperature, etc.

[Justification For Plurality Of Vessels & Measurements] In the development, optimisation, scale-up and design of crystallisation processes, it is desirable to understand the range of conditions under which crystals will grow, while avoiding conditions that result in primary nucleation. Unfortunately, this data is often unavailable as the necessary experimental work is typically time consuming and labour intensive to perform. Experimental methods for the determination of solubility curves and metastable zone widths are well established in the prior art. For example, start with a saturated solution of a material in a solvent system, cool until the cloud point is observed, then heat until the clear point is observed. Additional solvent can then be added and the process repeated until data has been collected at sufficient starting concentrations to adequately characterise the solubility curve and metastable zone width. Slow cooling rates must be used for the determination of solubility curves in order to allow the system to approach equilibrium. In addition, as the metastable zone width is known to be dependent on cooling rate, it should be determined at a variety of cooling rates and extrapolated to infinitely slow cooling. Additionally, as all measurements are subject to a degree of experimental error, it is good practice to replicate all measurements. As a result, sequential experimentation for the generation of solubility curves and metastable zone widths is very time consuming. Furthermore, it is often desirable to understand the impact of changing the solvent system, the presence of impurities, or the degree of agitation on the solubility curve and metastable zone width. It is therefore apparent that considerable time and expense can be saved if these experiments are performed in parallel, in a plurality of vessels, at a plurality of conditions e.g. a variety of concentrations of material, a variety of cooling rates, a variety of solvent ratios for multiple solvent systems, a variety of impurity profiles and a variety of stirring rates. It is known from the prior art that an automated parallel reactor systems, with e.g. a temperature control system and an optical sensor for determining the suspended solids present in a sample, can assist in reducing the time and expense of collecting this data.

[Justification For Automated & Online Analysis] Performing parallel solubility experiments for the determination of solubility curves and metastable zone widths in a plurality of vessels and at a plurality of conditions generates large quantities of data. Automating the analysis of this data saves time and expense and therefore makes more comprehensive investigations of solubility and crystallisation behaviour feasible. Furthermore, performing this data analysis while the experiments are running allows modifications to be made to the experimental programme. Automating control of the experimental programme may allow run times to be shortened or the quality of experimental results to be improved e.g. saving time by detecting the maximum dissolution temperature and minimum crystallisation temperature across multiple samples and adjusting temperature programs accordingly, improving quality by finding the optimal heating and cooling rates by reducing these rates until changes in cloud point and clear point can no longer be detected, improving quality by repeating experiments with ambiguous results. Furthermore, automating the post processing and reporting of the data e.g. by fitting curves, producing plots and providing interpretation advice, makes this data more accessible and allows the broader use of solubility curves and metastable zone width data in the development of crystallisation processes.

[The Method] The method according to the invention for determining the solubility curve and metastable zone width of a substance in a solvent system, comprises:
a) providing a sample comprising an amount of the substance and an amount of the solvent system;
b) altering the temperature of the sample;
c) measuring an optical parameter of the sample in relation to the temperature of the sample; and
d) determining the clear points and cloud points of the sample from a change of the optical parameter of the sample as a function of the temperature.
e) performing steps a), b), c) and d) for two or more samples varying the amount of the substance or the amount of the solvent system.

For the method according to the invention, similar advantages and preferred embodiments are applicable as for the system according to the invention.

In the context of this document, a solvent system may comprise a liquid mixture of one or more solvents, antisolvents, salts, impurities, surfactants, excipients or other additives. For a given solid substance, a solvent system is able to dissolve a portion of the solid substance.

Given a sample of a solid substance immersed in a solvent system, the 'clear point' may be formed by the temperature at which all of the solid dissolves, keeping the pressure and the overall composition of the combined system constant. The clear point may be considered a thermodynamic property of the system. Clear point temperatures determined for different concentrations of dissolved solid substance may lie on the 'solubility curve'.

Given a sample of a solid substance fully dissolved in a solvent system, the 'cloud point' may be formed by the temperature at which the first solid appears, keeping the pressure and the overall composition of the combined system constant. The cloud point is not a thermodynamic property of the system as it depends on, for example, the cooling rate. Cloud point temperatures determined for different concentrations of dissolved solid substance may lie on the 'supersolubility curve' or 'metastable limit', forming the boundary of the metastable zone (MSZ).

BRIEF DESCRIPTION OF THE DRAWINGS

An Embodiment Of The System

Further features, advantages and preferred embodiments of the system and method according to the invention will now be described with reference to the appended drawing, showing a non-limiting embodiment of the invention, in which.

DETAILED DESCRIPTION OF PREFERRED EMBODIMENTS

Figure 1:
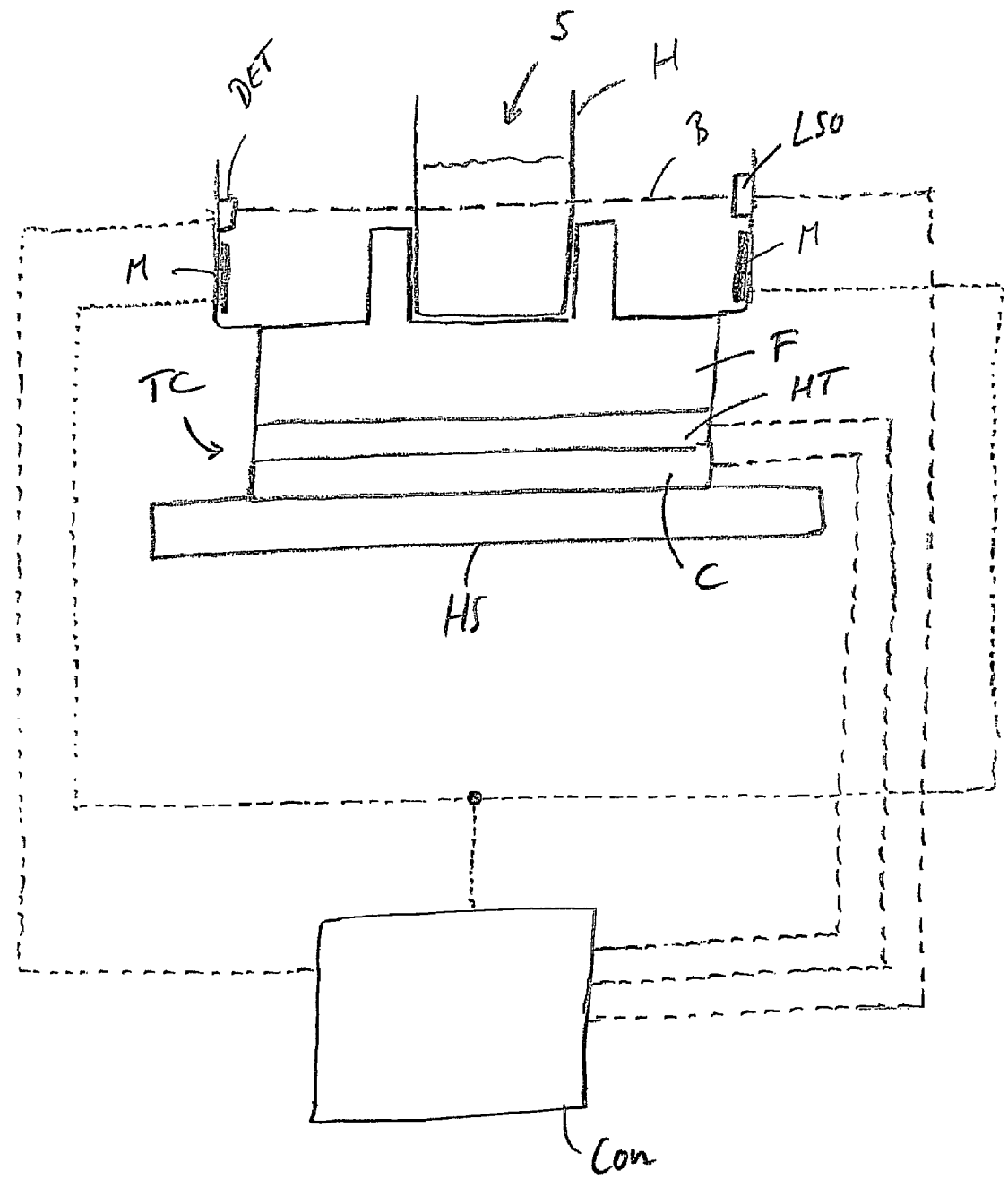
FIG. 1 schematically depicts a system for determining solubility according to an aspect of the invention.

FIG. 1 depicts a system for determining solubility curves and metastable zone widths according to an aspect of the invention. The system as depicted in FIG. 1 comprises a holder H to hold a sample S, the sample comprising a suitable amount of the substance and a suitable amount of the solvent system. The substance may comprise any inorganic or organic compound, e.g. a drug, that exists in the solid state at the operating pressure and the lowest operating temperature of the system and that can be dissolved by a suitable solvent system. A suitable solvent system may comprise any solvent or mixture of solvents able to dissolve the substance at the operating pressure and over the experimental temperature range, remaining substantially in the liquid state over this temperature range, and being substantially optically transparent over the wavelength band of the optical measurement device. The system further comprises a temperature conditioner TC to alter a temperature of the sample. In this example, the temperature conditioner TC is located below the holder H and is in thermal contact therewith via a fixation means F which further functions to keep the holder H holding the substance at a substantially fixed position. The holder H may be a separate part, i.e. may be taken out of the fixation means F. Preferably, the fixation means F comprise a material having a high thermal conductivity to arrange for a good thermal contact between the temperature conditioner TC and the substance as in the holder H. In this example, the temperature conditioner comprises a heater HT (e.g. comprising an electrical heater) and a cooling element C (e.g. comprising a Peltier element, heat exchanger or any other cooling means). The system may further comprise a heat sink HS e.g. a chiller, to operate in conjunction with the temperature conditioner TC. By means of the heater HT and the cooling element C, a temperature of the sample S in the holder H may be increased by the heater HT as well as reduced by the cooling element C. Both the heater HT and the cooling element C are under control of a control device CON.

Further, some electronic components of e.g. the control device or the optical parameter measurement device may be situated in a location that experiences low temperatures during operation of the system. In a humid atmosphere this may result in condensation of water on these components and result in failure or the impaired performance of these devices. The inventors have therefore devised to prevent this by connecting the system to a dry gas supply e.g. nitrogen, and so maintain a dry atmosphere around vulnerable components.

The control device may comprise any programmable device, such as a micro-controller, microcomputer etc. The control device may be integrated into the same device in which the holder, temperature conditioner etc. is comprised, however it may also be possible that—at least a part of—the control device is comprised in a separate device, e.g. a personal computer, etc. The control device may consist of dedicated hardware, however in a practical embodiment the control device may comprise a programmable device such as a micro-controller, microprocessor, personal computer etc. that is provided with suitable software instructions to perform the steps as described here. The control device may also consist of a plurality of micro-processors, microcontrollers, personal computers etc. each being provided with suitable software to enable these devices as a whole to perform the functions as described here, the micro-controllers, micro-processors, etc. being interconnected via any communication means, such as a serial connection such as a universal serial bus, or any other data connection means such as a computer network, e.g. an Intranet or an Internet.

The system further comprises an optical measurement device to measure an optical parameter of the sample S. In this example, the optical measurement device comprises a light source LSO such as a light emitting diode (LED) a laser diode, a filament lamp, a gas discharge lamp or any other light-emitting device. The light source LSO provides in operation for a light beam B travelling through a part of the sample S in the holder H. To this end, the holder H may at least partially be comprised of a material having a high transparency over the wavelength band of the optical measurement device. The light beam may comprise visible light, however also infrared light or ultraviolet light may be used. A part of the light of the beam may in operation be received by a detector DET. In this embodiment, the light source LSO is directed through the sample towards the detector DET i.e. a beam emitted by the light source LSO will travel towards the detector DET. The light source LSO and the detector DET are both connected to the control device CON, as symbolically indicated by the dotted lines between the control device CON and the light source LSO and detector DET respectively. In this embodiment, the light source LSO and detector DET perform (under control of the control device CON) a transmissivity measurement, i.e. transmissivity of the sample S is detected. Thereto, an amount of light (i.e. visible light, infrared light or ultraviolet light) is transmitted in a form of the beam B to the sample S in the holder H. Depending on a the turbidity of the sample, a larger or smaller part of the light of the beam may be absorbed, scattered, reflected etc. by the sample S, causing a remainder of the beam B to reach the detector DET. An advantage of this configuration is that use may be made of very low cost components such as a light emitting diode for the light source LSO and a photo diode or other low cost photo detector for the detector DET. Also, advanced optics may be omitted, as the configuration as described here showed to be relatively intolerant for manufacturing tolerances, deviations etc. of the detector DET, light source LSO as well as alignments thereof. In this example, the system further comprises a stirrer, more particularly in this example a magnetic stirrer (not shown) which will be submerged in the sample S. The magnetic stirrer may be driven by magnets M, such as in this example electro magnets generating a rotating or otherwise varying magnetic field. Thereto, the magnets M are under control of the control device CON, as indicated by the dotted lines between the electro magnets M and the control device CON. The operation of the system according to FIG. 1 will now be described with reference to FIGS. 2-4 and in particular with reference to FIGS. 3 and 4.

Operation Of The Embodiment

Figure 2:
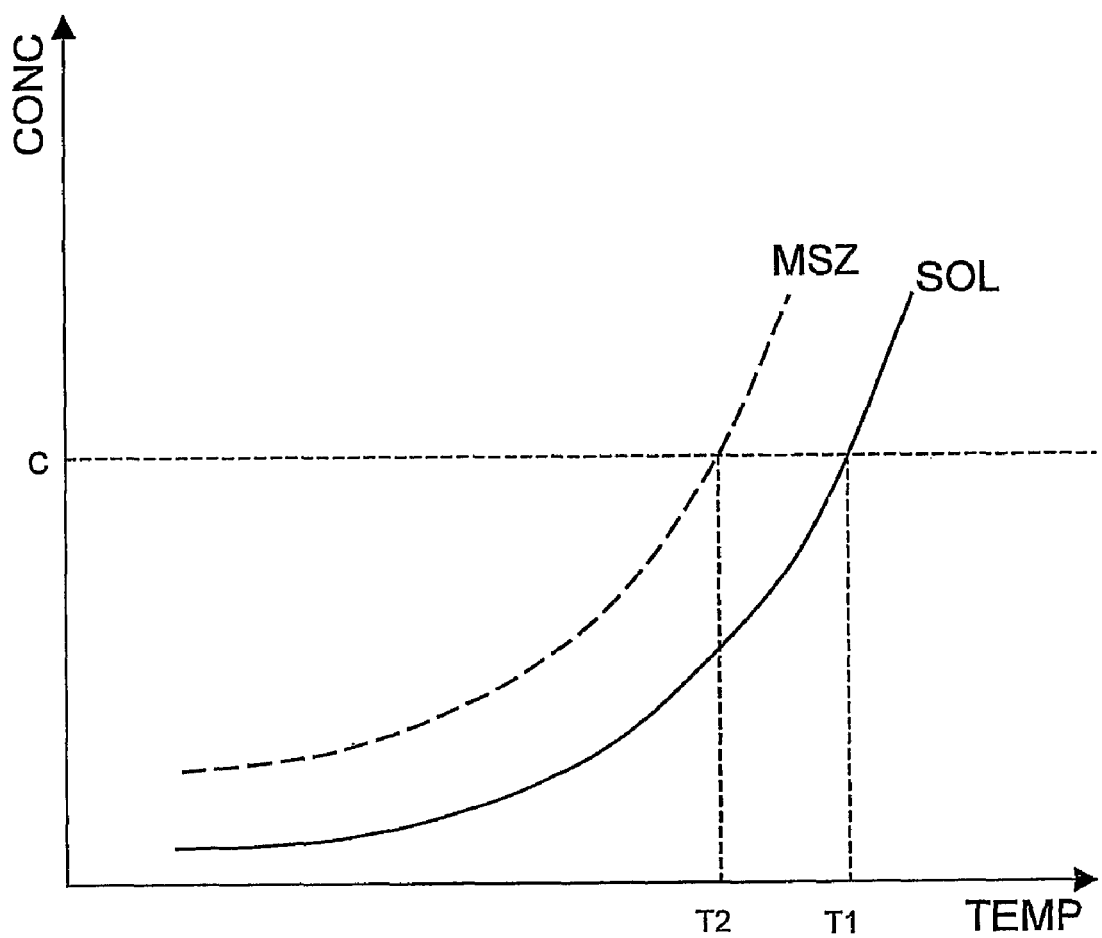
FIG. 2 depicts an example of a solubility curve and metastable zone width.

With reference to FIG. 2, given a sample of a substance dissolved in a solvent system that consists of a saturated solution of the substance of concentration C at temperature T1, cooling this solution at a given cooling rate will result in spontaneous crystallisation if cooled beyond temperature T2, i.e. the cloud point, on the metastable zone boundary MSZ. In other words, at the MSZ boundary curve a transition occurs from a state where the substance is dissolved to a state where a portion of the substance is undissolved. Given a sample where the concentration of material dissolved in a solvent system is C at temperature T2 and where a portion of the substance is undissolved, heating this sample at a sufficiently slow heating rate results in complete dissolution of the sample if heated beyond temperature T1, i.e. the clear point, on the solubility curve SOL. In other words, at the solubility curve, a transition occurs from a state where a portion of the substance in the sample is undissolved to a state where the substance is fully dissolved.

Figure 3A:
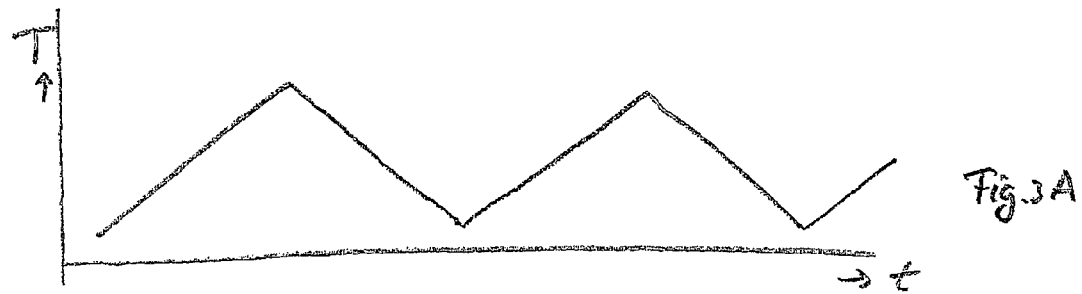
FIG. 3A-3C depict graphical views of the determination of cloud points and clear points in various stages of a procedure to be followed by the system and method according to an aspect of the invention.
Figure 3B:
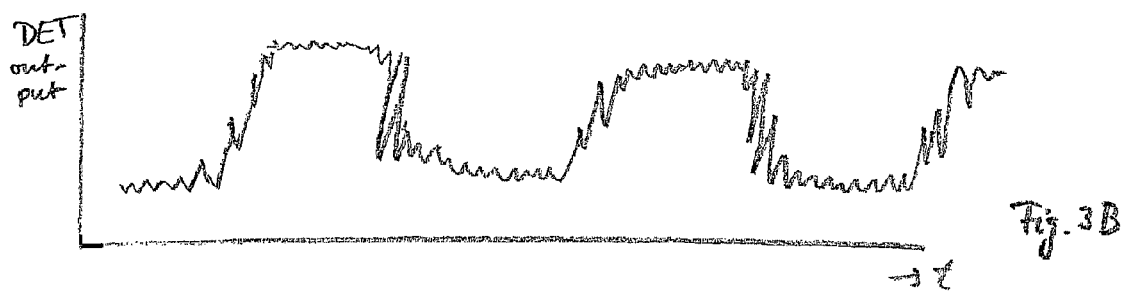

Operation of the system, and preferred embodiments thereof will now be described with reference to FIG. 3a-3c. FIG. 3a shows a graphical representation of the temperature T of a sample S held by the holder H in FIG. 2. On the horizontal axis of FIG. 3a-3c the time t is depicted. In FIG. 3a, the temperature T is on the vertical axis. FIG. 3a shows that the temperature is cycled, in this example the temperature follows a cycle comprising a linear increase followed by a linear decrease of the temperature. Due to the cycling of the temperature, the substance in the sample will alternately dissolve and crystallise, as the solubility and crystallisation behaviour of the substance in the solvent system shows a temperature dependency as depicted in FIG. 2. FIG. 3b shows the output signal of the light detector DET according to FIG. 1. Due to the alternating crystallisation and dissolution, the transmissivity of the sample alternately changes: when the substance dissolves, transmissivity increases, and therefore the output of the detector DET increases, while when crystallisation occurs, transmissivity decreases and therefore the output of the detector DET decreases. As shown in FIG. 3b, the output signal of the detector DET commonly shows a substantial amount of noise, or other disturbances. These may be due to a variety of reasons, e.g. bubbles of air in the sample, inhomogenities in the sample due to imperfect stirring, fluctuations in the output of the light source, electrical noise from the detector and/or amplifier that amplifies the detector output signal, as well as many other reasons. Many methods for reducing this noise by modifying the design of the optimal measurement device are known from the prior art. However, the inventors have opted instead to make use of simple, low cost, light emitter and detector hardware and use signal processing techniques to compensate for the noise and other disturbances.

The output signal of the detector may be subject to a number of signal processing and data analysis steps that may be performed by the control device CON, according to FIG. 1. These steps may include:

- sa) Smoothing the output signal of the detector (i.e. smoothing the measured optical parameter data)
- sb) Differentiating the smoothed detector output signal (i.e. differentiating the smoothed measured optical parameter data).
- sc) Identifying peaks in the differentiated smoothed detector output signal.
- sd) Identifying prolonged positive or negative sequences in the differentiated smoothed detector output signal.

The smoothing step (sa) may comprise application of an analog or digital signal smoothing or low-pass filtering method. Many such methods are known from the prior art. Analog smoothing or filtering may be implemented as e.g. an electronic circuit. Digital smoothing or filtering may be implemented by e.g. a digital signal-processing chip or in software running on a computer. Acausal filters and smoothing methods are preferred as they prevent time shifts in the signal, however, causal filters e.g. Finite Impulse Response and Infinite Impulse Response filters, may also be used. Suitable acausal digital filters and smoothing methods include e.g. moving window averaging, Savitzky-Golay filters, Fourier domain filters and wavelet smoothing.

The differentiation step (sb) may be performed by simply differencing the signal, however it is known from the prior art that more reliable results are obtained using e.g. a two-point central difference formula. Furthermore, steps (sa) and (sb) may be combined, resulting in a smoothing derivative filter e.g. a Savitzky-Golay derivative filter. In particular, the inventors have devised that a Gaussian smoothing derivative filter provided adequate results.

Figure 3C:
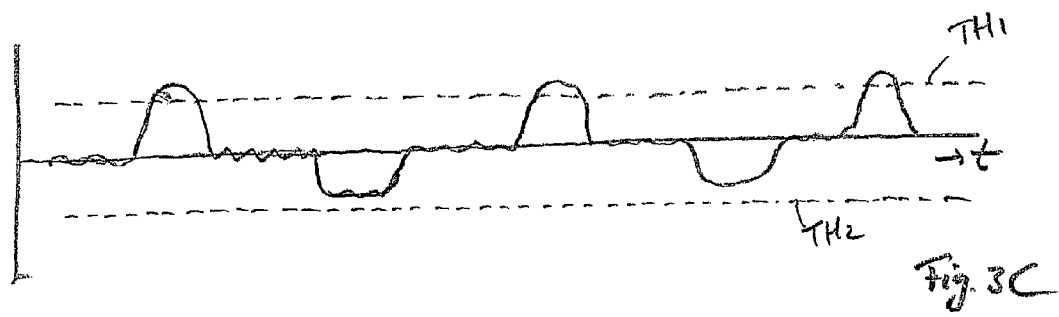

The smoothed differentiated detector output data is depicted in FIG. 3c. It may be noted that the noise has been reduced to a large extent. Furthermore, due to the differentiation, a rise or fall in the detector output may be easily identified, as a rise leads to a positive signal in FIG. 3c while a fall leads to a negative signal. Also, it may be observed that the rises and falls in the detector output, corresponding to dissolution or crystallisation transitions (see FIG. 3b), are typically relatively steep, thus leading to relatively high peaks in the signal after differentiation, as shown in FIG. 3c.

Finding peaks in the smoothed derivative of the detector output data identifies the location of steps or steep slopes in the transmissivity signal that may correspond to dissolution or crystallisation transitions. The peak identification step (sc) may be performed by:

- (i) Bracketing peaks by identifying portions of the signal that exceed predetermined threshold values in either a positive or negative directions. This is illustrated in FIG. 3c, with threshold values being indicated by the dotted lines TH1, TH2.
- (ii) Using a differentiation method, such as those discussed previously, to calculate a smoothed second derivative of the detector output data for at least the portions of the signal identified as bracketing peaks in step (i).
- (iii) Finding the peak position by scanning the portions of the signal identified in (i) for a change in the sign of the smoothed second derivative of the detector output data.

Step (i) excludes low magnitude peaks that, in practice, may result from imperfect smoothing or slow upward or downward drifts in the signal caused by phenomena other than dissolution and crystallisation.

Finding prolonged positive or negative sequences in the differentiated smoothed detector output signal, step (sd), identifies the location of slopes in the transmissivity signal that may also correspond to dissolution or crystallisation transitions. It has been noted that dissolution transitions can often take longer than crystallisation transitions and can therefore appear as gentle slopes in the transmissivity signal rather then steps.

It is recognised that it may also be possible to combine steps (c) and (d) by setting a lower threshold in step (sc) (i), finding areas under the signal by means of a numerical integration method e.g., Simpson's method, and determining whether the areas exceed a predetermined level. Using this method, large narrow peaks, corresponding to steps, may be detected as well as prolonged positive or negative sequences of low magnitude, corresponding to slopes.

In addition to noise, the output signal from the detector may also include artifacts, i.e. large, short term, spikes in the signal that are not due to a corresponding change in the transmissivity of the solution. These artifacts may be caused by e.g. the magnetic stirrer crossing the light beam. Furthermore, there is typically a start-up period at the beginning of a run where e.g. the temperature is coming to set-point, and the detection of transitions may not be reliable. In addition, the smoothing process may corrupt the beginning or end of the signal. It is also difficult to verify that transitions very close to the beginning or end of the signal are not due to artifacts. The positions of the candidate transitions identified in steps (sc) and (sd) may therefore be checked using a number of rules, with the aim of identifying transitions associated with artifacts or end effects, allowing these to be excluded e.g. are transitions too close together, too close to the beginning or end of the signal, is the temperature changing in the right direction.

When the transitions in the detector output signal have been found, the corresponding transition temperatures can be retrieved from the temperature profiles, illustrated in FIG. 3a. Thus, the temperature at which cloud point and clear point transitions occurred can be determined.

When a plurality of cycles, i.e. increases and decreases in temperature have been performed, averaging may be performed to increase the reliability of the estimates of the cloud point and clear point temperature and the precision of these measurements quantified. The measurements may e.g. be performed while varying one or more parameters such as the concentration of the substance in the solvent system, the composition of the solvent system, the speed of stirring, the rate of increase and decrease of temperature, the addition of further substances, or any other parameter.

[Fitting And Plotting Curves] Once measurement results have been obtained as described above, and the steps as described above performed for two or more samples varying in the concentration of substance only, solubility and metastable zone boundary curves may be determined for these samples. A line or curve may be fit to the cloud point temperature and concentration data measured at two or more concentrations of substance. This curve is then an experimentally determined approximation to the solubility curve, depicted as SOL in FIG. 2. Similarly, a line or curve may be fit to the clear point temperature and concentration data measured at two or more concentrations of substance. This curve is then an experimentally determined approximation to the metastable zone boundary curve, depicted as MSZ in FIG. 2.

From the prior art, it is known that many functions may be suitable for curve fitting e.g. linear, polynomial or exponential. In addition, various thermodynamically inspired equations e.g. a van t'Hoff equation, may also be used for this purpose. The parameters of these functions may be determined from the experimental data by minimising the sum of the squared error between the fitted curve and the experimental data using e.g. linear least squares or nonlinear least squares. Alternatively, other objective functions and fitting algorithms may be used to determine suitable parameter values e.g. Bayesian methods. Additionally, statistical tests may be performed to detect and exclude outliers from the fitting. Furthermore, based on e.g. the number of available data points and the distribution of these data points it may be possible to select an appropriate function type for fitting the experimental data. Alternatively, the parameters for a number of different function types could be to be fitted and the lack of fit compared to select the most appropriate curve type. This curve fitting may be substantially automated, producing plots and providing statistical interpretation advice that makes this data more accessible and so allowing broader use of solubility curves and metastable zone width data in the development of crystallisation processes. The control device CON, according to FIG. 1, may perform the curve fitting operations described above.

[Calibration] The system as described here may be calibrated according to a procedure, which will be described below. It may be possible to increase the temperature of the sample to a level at which the substance is substantially dissolved in the solvent system. Then, the optical parameter, in this example the transmissivity, may be calibrated. In other words a transmissivity of the sample as obtained at that temperature may be set to e.g. 100%. Then, measurements may be performed making use of a temperature range (in which e.g. a cyclical changing of the temperature is applied) which extends at least below the temperature at which the calibration has been performed. An advantage is that in this manner a sample calibration is made possible as at the relatively high temperature at which the calibration is performed, it is highly likely that the substance is fully dissolved in the solvent system. Therefore, a higher transmissivity of the sample than the transmissivity as found during the calibration is unlikely to occur. By now decreasing the temperature from the temperature at which the calibration has been performed, crystallisation may occur thus reducing the transmissivity and hence the output of the detector. Thus, calibration may be performed at a maximum detector output signal. An advantage of this type of calibration is that it may be performed e.g. before each temperature cycle, etc. or with suitable intervals. As an example, it may be possible to perform this calibration before each cycling of temperature, e.g. each time when a new sample is tested by the system. Thereby, accuracy of the transmissivity measurements may be increased, as parameters such as different properties of the sample (due to chemical composition, quantity, etc.) may be accounted for by the calibration, e.g. of each sample before the measurement on that sample is initiated. The calibration may comprise changing an optical output power of the light source LSO (or in general words the optical power source) until a power level has been reached at which a nominal maximum power is received by the detector. The detector detects the remainder of the optical output power (i.e. the remainder of the beam) transmitted through the sample in FIG. 1. As described above, when performing measurements, transmissivity will at maximum be equal to a transmissivity of the sample at the temperature at which the calibration has been performed. Thus, the detector output will be at maximum equal to, and possibly lower than the output as found during calibration. To benefit as much as possible from the dynamic range of the detector, it is advisable to set the output power of the light source such that with the given sample, the detector receives a maximum amount of optical energy. Thus, with a relatively clear sample having a high transmissivity, output power may be set lower than with a sample that has a relatively low transmissivity. By adapting the output of the light source to the sample, accuracy may be increased, as detector noise or detector amplifier noise, stray light effects etc. may be reduced as regards to the effect thereof, by ensuring that the signal received by the detector is as near as possible to the maximum nominal signal to be received by the detector.

[Plurality Of Vessels] To increase the throughput of the system i.e. to be able to perform as many experiments, measurements etc. as possible within an as short a time frame as possible, the system may comprise a plurality of holders to hold a plurality of samples, the control device thereby being arranged to perform the process as described here preferably in parallel for the plurality of samples. Each of the holders may be provided with an individual temperature control means TC, however it is also possible that a group of holders, e.g. a row of holders is held at a same temperature by a common temperature control means TC. The holders may be set up in a row, matrix etc. The holder may have any form or shape. It is possible that, in the example where multiple samples are tested by the system in parallel, separate holders are used for each of the samples, however as an alternative it may equally well be possible that holders are applied in which a plurality of different samples may be contained, e.g. a so-called chip holder—i.e. a card made of a material such as a glass, the card comprising an array of miniature holes, each hole serving as a holder for a sample. In such a configuration, the light source and detector may, instead of being positioned as depicted in FIG. 1, be positioned such that the beam B travels vertically through the sample to be tested. Thereby, interference by nearby samples may be prevented. The build up of the system according to FIG. 1 may be cost effective: the detector and light source may be positioned on a printed circuit board, which e.g. surrounds the sample, the printed circuit board also carrying electric conductors which form part of the electromagnets M as depicted in FIG. 1. The holder H may be exchangeable, thus be a separate part which can be taken out of the system, to enable the preparation of the next sample (or a batch of samples) during the time when tests are performed on a particular sample (or a batch of samples). Such an exchangeable holder H may be disposable, so eliminating the necessity for cleaning.

[Online Analysis & Programme Modification] Data analysis is typically performed once an experiment is complete. However, performing automated data processing and identification of the dissolution and crystallisation transitions, as described above, while a run is still progressing, allows modifications to be made to the experimental programme. This may allow run times to be shortened or the quality of experimental results to be improved. The control device CON, according to FIG. 1, may perform the control of the experimental programme, a number of examples of which are described below.

[Adjusting Temperature Programme Online] For example, when cycling the temperature, at a certain moment a crystallisation or dissolution transition may be detected, then a further change of the temperature in the direction in which it just has changed, may be superfluous. At that moment, the control device may control the temperature control means to reverse the direction of change of the temperature thus saving time by shortening a temperature cycle. In the case where a group of samples is held at the same temperature by a common temperature control means, a maximum dissolution temperature and minimum crystallisation temperature could be determined online for these samples and the temperature program adjusted, as described, to eliminate superfluous temperature changes.

[Identifying Optimal Heating Rate Online] As a further example, it is known from the prior art that accurate determination of the solubility curve requires a sufficiently slow heating rate to approach thermodynamic equilibrium. In order to efficiently determine a fastest suitable heating rate, the control device may control the temperature control means to reduce the heating rate on successive temperature cycles and stop the programme when the clear point temperatures, as detected by the online analysis, stop changing within some predefined tolerance.

[Identifying Optimal Cooling Rate Online] In addition, the location of the metastable zone boundary may be dependent on the cooling rate. It is therefore often desirable to determine the metastable zone boundary at a number of cooling rates sufficient to allow extrapolation to an infinitely slow cooling rate. In order to allow accurate extrapolation to an infinitely slow cooling rate, the control device may e.g. control the temperature control means to reduce the cooling rate on successive temperature cycles; fit a function e.g. a line or curve, to the experimentally determined cloud point temperature and cooling rate data determined by online analysis after each cycle; estimate from the fitted function the cloud point temperature extrapolated to an infinitely slow cooling rate; estimate the error of the predicted cloud point temperature at an infinitely slow cooling rate and; determine whether this error falls within some predefined tolerance; stopping the programme when the cloud point at an infinitely slow cooling rate can be estimated to within a predefined error tolerance.

[Online Replicate And Outlier Detection] The control device may also determine a precision of the measured data. In the case that a substantial amount of variation between measurements is identified, then this may be an indication for the control device to perform more measurements, e.g. perform more temperature cycles. If however consecutive measurements appear to be within a relatively narrow tolerance, then the control device may be programmed to stop the programme, as in that case performing additional measurements may waist time, while not providing additional information.

Further, the control device could be programmed to check for outliers during a run, e.g. measurements that deviate from data found at the same conditions in a previous cycle, a previous sample, etc. or any other comparable or similar experiment or cycle, and decide to redo this experiment or not take into account result thereof. Thereby, erroneous measurement obtained by the control device could be excluded from the analysis to avoid any negative consequences thereof in the interpretation of the experiments. A similar mechanism could also be used in case that multiple detectors are applied, e.g. a transmissivity detector and a scattering detector as described below. The control device could decide which detector to take into account: in case of strange or erroneous data (which could e.g. be due to the stirrer which intersects with the beam), then the control device could be programmed to not take into account some of the data provided by the detectors. Similar mechanisms as described above may be used here for e.g. comparing the data with previous data or later data, comparing the data with an average, etc. Also, a relation between the transmissivity data and scattering data may be taken into account.

Further, it may be possible that the control device is programmed to take account of a goodness of fit of the fitted solubility or metastable zone boundary curve. Suppose that a solubility curve as depicted as SOL in FIG. 2 is to be obtained as a result of the experiments. Experiments may e.g. be performed with a discrete amount of concentrations of the substance in the solvent system. Then, a curve may be fit to the results, as described above. In the case that the curve fitting would show a certain amount of error, or in the case that an erroneous data points have been found, the control device could be programmed to redo part of the experiments or to suggest other concentrations etc. to obtain additional data points to allow the curve to be fit with a greater certainty with respect to e.g. the standard error.

AN EMBODIMENT OF THE METHOD

Figure 4:
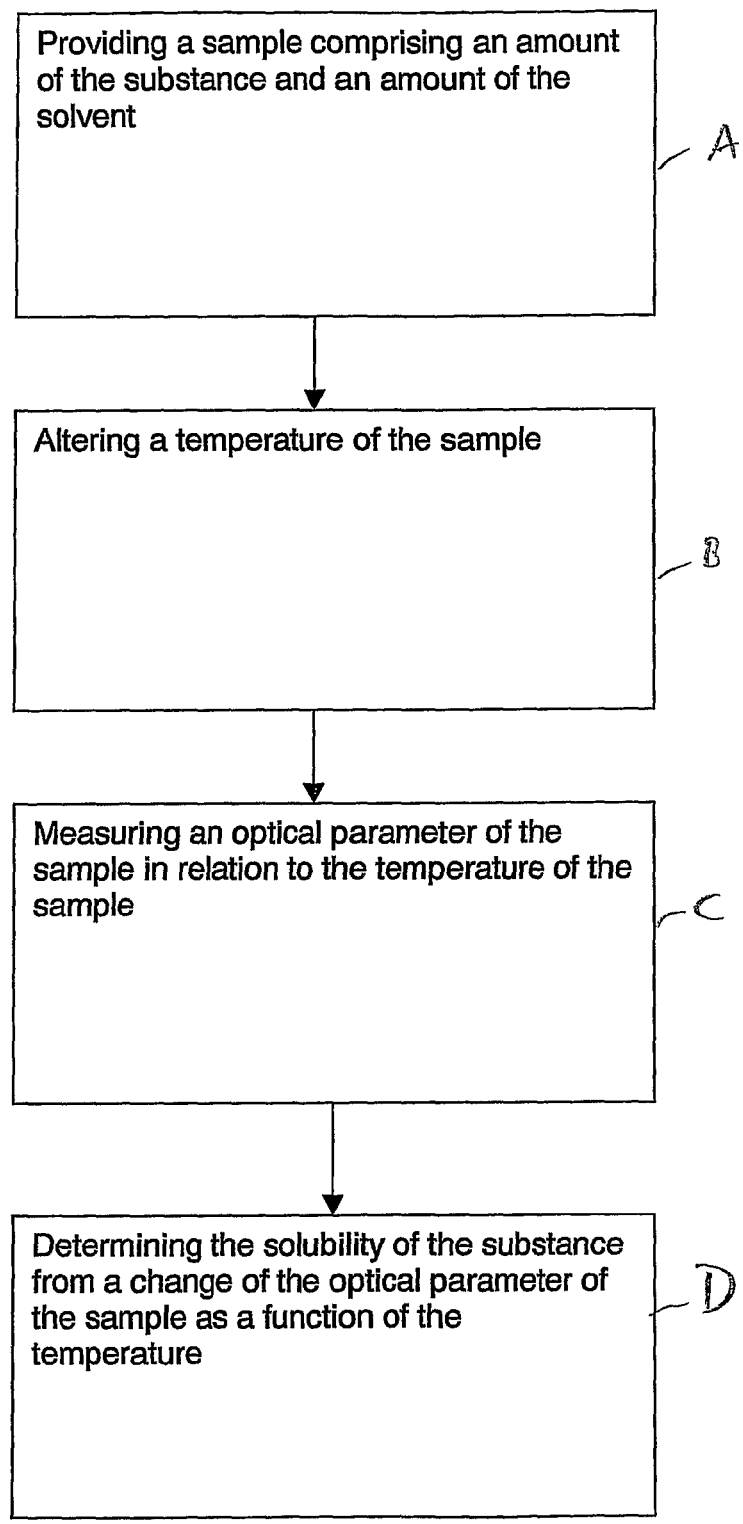
FIG. 4 depicts a flow diagram of the method according to an aspect of the invention.

The method according to the invention will now be described with reference to FIG. 4. According to the method, a sample is provided which comprises an amount of the substance and an amount of the solvent system, as depicted in A. Then, the temperature of the sample is altered as depicted in B. Next, an optical parameter of the sample is measured in relation to the temperature of the sample, as depicted in C. Then, as depicted in D, the cloud point and clear point of the sample is determined from a change of the optical parameter of the sample as a function of the temperature. For the method according to the invention, the same or similar advantages apply as for the system according to the invention which has been described above, also the same preferred embodiments as described with reference to the system according to the invention, the same or similar alternatives, further developments etc. are possible providing same or similar advantages as described above. The method as described here may be practised making use of the system as described above with regard to FIGS. 1 and 3a-3c.

In addition to the embodiments as described above, further improvements or variations will be described below.

[Identifying Polymorphic Transformation] Further, in the sample, polymorphic transformations may occur. Different polymorphs of the same substance may have different physical properties, including solubility. Therefore, if the dominant polymorph changes during the course of an experiment, the solubility and metastable boundary curves, depicted in FIG. 2, may exhibit a discontinuity. e.g. at a lower temperature, polymorph A may be dominant, thus experiments providing solubility data as regards to polymorph A, while at a higher temperature another polymorph B may be dominant in the sample, thus providing solubility data thereof. In such a case, it may be advisable to perform a larger number of experiments to obtain sufficient data points to provide for an accurate solubility curve e.g. fitting a solubility curve as a piecewise linear function with a discontinuity at the polymorphic transformation. With the invention described herein, performing a large number of experiments may be facilitated by utilising a plurality of vessels, performing multiple experiments in parallel and substantially automating the experimentation and data analysis.

[Scattering Measurement] Further, it may be possible to apply a scattering measurement instead of the transmissivity measurement as described above. Also, a combination of a transmissivity measurement and a scattering measurement may be applied. In that case, use may be made of a single light source LSO, wherever using two or even more detectors, one detector being positioned in a direction of the beam, thus measuring a transmissivity as has been discussed above, while one or more other detectors are positioned off-axis, thus providing scattering data, i.e. the more scattering occurs in the sample (due to e.g. crystallisation), the more output will be provided by these detectors.

[Liquid Dispensing] Further, it may be possible to add a liquid dispenser to the system e.g. a liquid dispensing robot, and program the addition of solvents or other materials by means of the control device. This would have the benefit of e.g. allowing measurements to be performed for a range of concentrations by successive dilution of the sample.

[Experimental Design] In an additional embodiment, the control device may run software that has been programmed to provide experimental design tools that assist a user of the system to design and analyse experiments for the determination for solubility curves and metastable zone boundary curves. This may include e.g. creating a combinatorial list of experiments at specified concentrations of material, solvent systems, cooling and heating rates.

The system and method according to the invention may be used for determining the clear point, the cloud point or both the clear point and the cloud point.

What is claimed is:

1. A system for determining a cloud point or a clear point of a substance in a solvent system, the system comprising:
   a holder to hold a sample comprising an amount of the substance and an amount of the solvent system,
   a temperature conditioner to alter the temperature of the sample,
   an optical measurement device to measure an optical parameter of the sample, and
   a control device to control at least the temperature conditioner and the optical measurement device, the control device being programmed to:
   a) alter the temperature of the sample by the temperature conditioner;
   b) measure the optical parameter of the sample by the optical measurement device; and
   c) determine the cloud point or clear point of the substance from a change of the optical parameter of the sample as a function of the temperature;
   wherein c) comprises:
   smoothing measured optical parameter data;
   differentiating the smoothed measured optical parameter data;
   detecting peaks in the differentiated, smoothed, measured optical parameter data, and
   associating positive peaks with candidate clear point transitions and negative peaks with candidate cloud point transitions.

2. The system according to claim 1, wherein a) comprises increasing the temperature to a level at which the substance is substantially dissolved in the solvent system, and calibrating the optical parameter prior to b).

3. The system according to claim 1, wherein a) comprises a cyclical changing of the temperature, the cyclical changing being performed over a temperature range extending at least below the temperature at which the calibration has been performed.

4. The system according to claim 1, wherein the smoothing and the differentiating are performed by a Gaussian smoothing derivative filter.

5. The system according to claim 1, wherein the smoothing and the differentiating are performed by a Savitzky-Golay smoothing derivative filter.

6. The system according to claim 1, wherein detecting peaks in the differentiated, smoothed, measured optical parameter data comprises finding portions of the differentiated, smoothed, measured optical parameter signal that exceed a predetermined threshold in a positive or negative direction and searching the identified portions of the signal to find points where a second derivative of the smoothed, measured optical parameter signal changes sign.

7. The system according to claim 1, wherein c) comprises:
   detecting portions of the differentiated, smoothed, measured optical parameter signal with a prolonged sequence of positive or negative values without a zero crossing, and
   associating positive sequences with candidate clear point transitions and negative sequences with candidate cloud point transitions.

8. The system according to claim 1, wherein c) comprises:
   finding areas under portions of the signal that exceed a predetermined threshold in a positive or negative direction by numerical integration,
   determining whether the areas exceed a predetermined level, and
   associating positive sequences with candidate clear point transitions and negative sequences with candidate cloud point transitions.

9. The system according to claim 1, wherein c) further comprises:
   applying rules to exclude illogical candidate transitions.

10. The system according to claim 9 wherein the rules comprise at least one of:
    excluding candidate transitions that are closer together than a predetermined time tolerance;
    excluding candidate transitions that are to the beginning or end of the signal than a predetermined time tolerance; and
    excluding candidate transitions for which the associated temperature change is in the wrong direction.

11. The system according to claim 9, wherein c) further comprises:
    determining cloud point or clear point temperatures associated with the remaining transitions.

12. The system according to claim 1, wherein, prior to performing the steps of claim 1, erroneous data points are excluded by a data point exclusion rule.

13. The system according to claim 1, wherein the optical parameter comprises at least one of a transmisivity and a scattering of optical light by the sample.

14. The system according to claim 1, wherein calibrating the optical parameter comprises changing an optical output power of an optical power source of the optical energy until a power level has been reached at which a nominal maximum power is received by a detector, the detector to detect a remainder of the optical output power transmitted through or scattered by the sample.

15. The system according to claim 1, comprising a plurality of holders to hold a plurality of samples, the control device being arranged to perform a) to c) for at least two samples in parallel.

16. The system according to claim 1, wherein the control device is further programmed to fit a function to:
    cloud point temperature and concentration data measured at two or more concentrations of substance, and
    clear point temperature and concentration data measured at two or more concentrations of substance.

17. The system according to claim 16 wherein the functions that may be fit comprise at least one of a linear, polynomial or exponential function, or a van t'Hoff equation.

18. The system according to claim 16 wherein the control device is further programmed to fit a number of different function types and select the most appropriate curve for representing the measured data.

19. The system according to claim 1, wherein the control device is further programmed to perform data analysis and assignment of cloud point and clear point transitions in real time, while measurements are being performed and make appropriate modifications to the experimental programme.

20. The system according to claim 19, wherein making appropriate modifications to the experimental programme comprises at least one of:
 determining a precision of the measured data from repeat measurements and perform additional replicates if the precision is low, or
 checking for measurements that deviate from data recorded at same conditions and replicate such experiments or not take these measurements into account during further analysis.

21. The system according to claim 19, wherein making appropriate modifications to the experimental programme further comprises at least one of:
 determining maximum dissolution and minimum crystallisation temperatures of one or more samples during a run and adjusting the temperature programme to eliminate superfluous temperature changes in future temperature cycles;
 determining a fastest suitable heating rate by reducing the heating rate on successive temperature cycles and stopping the programme when the clear point temperatures, as detected by the online analysis, stops changing within some predefined tolerance;
 determining the cloud point at an infinitely slow cooling rate by reducing the cooling rate on successive temperature cycles; fitting a curve to the experimentally determined cloud point temperature and cooling rate data determined by online analysis after each cycle; extrapolating the cloud point temperature to an infinitely slow cooling rate; estimating the prediction error at an infinitely slow cooling rate and; determining whether this prediction error falls within some predefined tolerance; stopping the programme when the cloud point at an infinitely slow cooling rate can be estimated to within a error tolerance; and
 determining a goodness of fit of fitted functions and replicate some of the experiments or suggest other concentrations etc. to obtain additional data points to allow the function to be fit with a greater certainty.

22. The system according to claim 1, wherein the control device is arranged to perform a) to c) for at least two samples to generate a cloud point curve and a clear point curve from results obtained from the samples at different concentrations of the substance in the solvent system.

23. A method for determining a cloud point or a clear point of a substance in a solvent system, the method comprising:
 a) providing a sample comprising an amount of the substance and an amount of the solvent system,
 b) altering a temperature of the sample,
 c) measuring an optical parameter of the sample in relation to the temperature of the sample; and
 d) determining the cloud point or clear point of the substance from a change of the optical parameter of the sample as a function of the temperature;
 wherein d) comprises:
  smoothing measured optical parameter data;
  differentiating the smoothed measured optical parameter data;
  detecting peaks in the differentiated, smoothed, measured optical parameter data, and
  associating positive peaks with candidate clear point transitions and negative peaks with candidate cloud point transitions.

24. The method according to claim 23, wherein b) comprises increasing the temperature to a level at which the substance is substantially dissolved in the solvent system, and calibrating the optical parameter prior to b).

25. The method according to claim 23, wherein b) comprises a cyclical changing of the temperature, the cyclical changing being performed over a temperature range extending at least below the temperature at which the calibration has been performed.

26. The method according to claim 23, wherein the smoothing and the differentiating are performed by a Gaussian smoothing derivative filter.

27. The method according to claim 23, wherein the smoothing and the differentiating are performed by a Savitzky-Golay smoothing derivative filter.

28. The method according to claim 23, wherein detecting peaks in the differentiated, smoothed, measured optical parameter data comprises finding portions of the differentiated, smoothed, measured optical parameter signal that exceed a predetermined threshold in a positive or negative direction and searching the identified portions of the signal to find points where a second derivative of the smoothed, measured optical parameter signal changes sign.

29. The method according to claim 23, wherein d) comprises:
 detecting portions of the differentiated, smoothed, measured optical parameter signal with a prolonged sequence of positive or negative values without a zero crossing; and
 associating positive sequences with candidate clear point transitions and negative sequences with candidate cloud point transitions.

30. The method according to claim 23, wherein c) comprises:
 finding areas under portions of the signal that exceed a predetermined threshold in a positive or negative direction by numerical integration,
 determining whether the areas exceed a predetermined level, and
 associating positive sequences with candidate clear point transitions and negative sequences with candidate cloud point transitions.

31. The method according to claim 23, wherein d) comprises:
 applying rules to exclude illogical candidate transitions.

32. The method according to claim 31, wherein the rules comprise at least one of:
 excluding candidate transitions that are closer together than a predetermined time tolerance;
 excluding candidate transitions that are to the beginning or end of the signal than a predetermined time tolerance; and
 excluding candidate transitions for which an associated temperature change is in a wrong direction.

33. The method according to claim 31, wherein c) comprises:
 determining cloud point or clear point temperatures associated with the remaining transitions.

34. The method according to claim 23 wherein, prior to performing the steps of claim 23, erroneous data points are excluded by a data point exclusion rule.

35. The method according to claim 23, wherein the optical parameter comprises at least one of a transmisivity and a scattering of optical light by the sample.

36. The method according to claim 23, wherein calibrating the optical parameter comprises changing an optical output power of an optical power source of the optical energy until a power level has been reached at which a nominal maximum power is received by a detector, the detector to detect a remainder of the optical output power transmitted through or scattered by the sample.

37. The method according to claim 23, wherein a plurality of holders is applied to hold a plurality of samples, the control device being arranged to perform a) to d) for at least two samples in parallel.

38. The method according to claim 23, further comprising fitting a function to:
cloud point temperature and concentration data measured at two or more concentrations of substance, or
clear point temperature and concentration data measured at two or more concentrations of substance.

39. The method according to claim 38 wherein the functions that may be fit comprise at least one of a linear, polynomial or exponential function, or a van t'Hoff equation.

40. The method according to claim 38 further comprising fitting a number of different function types and select the most appropriate curve for representing the measured data.

41. The method according to claim 23, further comprising performing data analysis and assignment of cloud point and clear point transitions in real time, while measurements are being performed and make appropriate modifications to the experimental programme.

42. The method according to claim 41, wherein making appropriate modifications to the experimental programme comprises at least one of:
determining a precision of the measured data from repeat measurements and perform additional replicates if the precision is low; or
checking for measurements that deviate from data recorded at the same conditions and replicate such experiments or not take these measurements into account during further analysis.

43. The method according to claim 41, wherein making appropriate modifications to the experimental programme further comprises at least one of:
determining maximum dissolution and minimum crystallisation temperatures of one or more samples during a run and adjusting the temperature programme to eliminate superfluous temperature changes in future temperature cycles;
determining a fastest suitable heating rate by reducing the heating rate on successive temperature cycles and stopping the programme when the clear point temperatures, as detected by the online analysis, stops changing within some predefined tolerance;
determining the cloud point at an infinitely slow cooling rate by reducing the cooling rate on successive temperature cycles; fitting a curve to the experimentally determined cloud point temperature and cooling rate data determined by online analysis after each cycle; extrapolating the cloud point temperature to an infinitely slow cooling rate; estimating the prediction error at an infinitely slow cooling rate and; determining whether this prediction error falls within some predefined tolerance; stopping the programme when the cloud point at an infinitely slow cooling rate can be estimated to within a error tolerance; and
determining a goodness of fit of fitted functions and replicate some of the experiments or suggest other concentrations etc. to obtain additional data points to allow the function to be fit with a greater certainty.

44. The method according to claim 23, wherein steps a)-d) are performed for at least two samples in parallel.

45. A software program comprising program instruction to perform the method according to claim 23, when loaded into a control device of a system comprising:
a holder to hold a sample comprising an amount of the substance and an amount of the fluid,
a temperature conditioner to alter a temperature of the sample,
an optical measurement device to measure an optical parameter of the sample, and
the control device to control at least the temperature conditioner and the optical measurement device.

46. The method according to claim 23, further comprising:
e) performing steps a), b), c) and d) for two or more samples varying the amount of the substance or the amount of the solvent system, to generate a cloud point curve and a clear point curve.

* * * * *